(12) United States Patent
Marcus et al.

(10) Patent No.: US 9,827,552 B2
(45) Date of Patent: Nov. 28, 2017

(54) FUNCTIONALIZED LIPID MODIFICATION OF SOLID PHASE SURFACES FOR USE IN CHROMATOGRAPHY

(71) Applicant: Clemson University, Clemson, SC (US)

(72) Inventors: R. Kenneth Marcus, Clemson, SC (US); Kenneth A. Christensen, Clemson, SC (US)

(73) Assignee: Clemson University, Clemson, SC (US)

( * ) Notice: Subject to any disclaimer, the term of this patent is extended or adjusted under 35 U.S.C. 154(b) by 443 days.

(21) Appl. No.: 14/333,561

(22) Filed: Jul. 17, 2014

(65) Prior Publication Data

US 2015/0024511 A1    Jan. 22, 2015

Related U.S. Application Data

(60) Provisional application No. 61/847,135, filed on Jul. 17, 2013.

(51) Int. Cl.
*B01J 20/00* (2006.01)
*B01J 20/281* (2006.01)
(Continued)

(52) U.S. Cl.
CPC .......... *B01J 20/281* (2013.01); *B01D 15/206* (2013.01); *B01D 15/3823* (2013.01);
(Continued)

(58) Field of Classification Search
CPC ..................................................... B01J 20/281
(Continued)

(56) References Cited

U.S. PATENT DOCUMENTS 5,200,248 A    4/1993    Thompson et al.
5,395,619 A    3/1995    Zalipsky et al.
(Continued)

OTHER PUBLICATIONS

Prakash K. Kandel, Lawrence P. Fernando, P. Christine Ackroyd and Kenneth A. Christensen "Incorporating functionalized polyethylene glycol lipids into reprecipitated conjugated polymer nano particles for bioconjugation and targeted labeling of cells" Nanoscale, 2011, 3, 1037-1045.*

(Continued)

*Primary Examiner* — Christine T Mui
*Assistant Examiner* — Emily Berkeley
(74) *Attorney, Agent, or Firm* — Dority & Manning, PA

(57) ABSTRACT

A solid phase for use in separation has been modified using an aqueous phase adsorption of a headgroup-modified lipid to generate analyte specific surfaces for use as a stationary phase in separations such as high performance liquid chromatography (HPLC) or solid phase extraction (SPE). The aliphatic moiety of the lipid adsorbs strongly to a hydrophobic solid surface, with the hydrophilic and active headgroups orienting themselves toward the more polar mobile phase, thus allowing for interactions with the desired solutes. The surface modification approach is generally applicable to a diversity of selective immobilization applications such as protein immobilization clinical diagnostics and preparative scale HPLC as demonstrated on capillary-channeled fibers, though the general methodology could be implemented on any hydrophobic solid support material.

9 Claims, 9 Drawing Sheets

(51) Int. Cl.
| | |
|---|---|
| G01N 30/50 | (2006.01) |
| G01N 33/543 | (2006.01) |
| B01J 20/28 | (2006.01) |
| B01J 20/285 | (2006.01) |
| B01J 20/32 | (2006.01) |
| B01D 15/20 | (2006.01) |
| B01D 15/38 | (2006.01) |
| C07K 1/20 | (2006.01) |
| G01N 30/88 | (2006.01) |

(52) U.S. Cl.
CPC ....... *B01J 20/285* (2013.01); *B01J 20/28023* (2013.01); *B01J 20/28052* (2013.01); *B01J 20/321* (2013.01); *B01J 20/3272* (2013.01); *B01J 20/3274* (2013.01); *B01J 20/3293* (2013.01); *C07K 1/20* (2013.01); *G01N 30/50* (2013.01); *G01N 33/54353* (2013.01); *G01N 33/54393* (2013.01); *B01J 2220/56* (2013.01); *G01N 2030/8813* (2013.01); *Y10T 436/255* (2015.01)

(58) Field of Classification Search
USPC .......................................................... 436/178
See application file for complete search history.

(56) References Cited

U.S. PATENT DOCUMENTS

| | | | |
|---|---|---|---|
| 5,972,505 A | 10/1999 | Phillips et al. | |
| 6,224,903 B1 | 5/2001 | Martin et al. | |
| 6,605,299 B2 | 8/2003 | Zalipsky | |
| 7,261,813 B2 | 8/2007 | Marcus et al. | |
| 7,374,673 B2 | 5/2008 | Marcus | |
| 7,740,763 B2 | 6/2010 | Marcus et al. | |
| 2006/0201881 A1* | 9/2006 | Marcus | B01D 15/08 210/635 |

OTHER PUBLICATIONS

Lutz Schmitt, Christian Dietrich, and Robert Tampe "Synthesis and Characterization of Chelator-Lipids for Reversible Immobilization of Engineered Proteins at Self-Assembled Lipid Interfaces" J. Am. Chem. SOC. 1994,116, 8485-8491.*

R. Kenneth Marcus, W. Clay Davis, Brad C. Knippel, LaTasha LaMotte, Teresa A. Hill, Dvora Perahia, J. David Jenkins "Capillary-channeled polymer fibers as stationary phases in liquid chromatography separations" Journal of Chromatography A, 986 (2003) 17-31.*

R. Kenneth Marcus et al.; "Head group-functionalized poly(ethyleneglycol)-lipid (PEG-lipid) surface modification for highly selective analyte extractions on capillary-channeled polymer (C-CP) fibers;" pp. 2027-2250; *Analyst*; vol. 139; No. 9; May 7, 2014.

Abby J. Schadock-Hewitt and R. Kenneth Marcus; "Loading charactersitics and chemical stability of headgroup-functionalized poly(ethylene glycol)-lipid ligand tethers on polypropylene capillary-channeled polymer fibers;" pp. 3595-3602; *Journal of Separation Science*; vol. 37; 2014.

* cited by examiner

FUNCTIONALIZED LIPID MODIFICATION OF SOLID PHASE SURFACES FOR USE IN CHROMATOGRAPHY

CROSS REFERENCE TO RELATED APPLICATION

This application claims filing benefit of U.S. Provisional Patent Application Ser. No. 61/847,135 having a filing date of Jul. 17, 2013, which is incorporated herein by reference in its entirety.

STATEMENT REGARD IN FEDERALLY SPONSORED RESEARCH OR DEVELOPMENT

This invention was made with government support under grant numbers 1011820, 0937985, and 1307078 awarded by the National Science Foundation. The United States government has certain rights in the invention.

BACKGROUND OF THE INVENTION

Liquid chromatography, which provides the ability to separate a fluid sample, for instance to purify or concentrate an analyte in a fluid sample, has proven to be of great assistance in a variety of analytical applications. For instance, the ability to assay the contents of test samples has proven extremely useful in the testing and examination of biological samples, in particular as analytical testing of biological samples often calls for a wide variety of tests and examinations from a starting sample of a very small volume. Polymeric stationary/support phases have been under investigation for over fifty years for use in liquid chromatography, e.g., high performance liquid chromatography (HPLC). Polymeric phases have been evaluated and implemented for the separation of ions, small molecules, and macromolecules. Common implementations of polymeric stationary phases can take a fibrous form including hollow or cylindrical solid fibers, rolled fabric, fiber staples, and continuous fiber phases, as well as the more common polymer beads/particulates and monoliths. These polymeric solid phases (used generically here to refer to polymeric stationary/support phases) generally offer common benefits over more widely applied porous silica-based stationary phases including chemical robustness and ease of chemical derivatization. Additional beneficial features of a polymeric fiber format include improved mass transfer due to the nonporous nature of the solid and convective diffusion throughout the column structure.

One specific type of fiber that has been described for use in liquid chromatography is the capillary-channeled polymer fiber (see, e.g., U.S. Pat. No. 7,740,763 to Marcus, et al.; U.S. Pat. No. 7,374,673 to Marcus, and U.S. Pat. No. 7,261,813 to Marcus, et al., all of which are incorporated herein by reference). Capillary-channeled polymer fibers have a unique shape as illustrated (as one example) in FIG. 1 that includes multiple channels that extend along the axial length of the fiber. The channels promote a self-alignment of the fibers when packed, for instance into an HPLC column, with interdigitation of the fibers (FIG. 2) resulting in a distribution of micron-sized open channels that run the length of the column. Capillary-channeled fibers can have two to three times more surface area in comparison to circular cross section polymer fibers of the same nominal diameter. The capillary channels of a column packed with the fibers are very efficient at fluid transport, allowing for traditional column sizes to be operated at high linear velocities while maintaining low back pressures. As a result, a column including capillary-channeled fibers can provide for high throughput and high efficiency separation, for instance separation of biomacromolecules.

While polymeric solid phase materials such as capillary-channeled fibers have provided great improvement to separation technologies, there remains a desire to perform more highly selective separations and extractions. Recent research has focused on the ability to modify the surface of the polymeric solid phase, allowing for more specific analyte-surface interactions. Modification has been approached to date through active end group generation methods including aminolysis, hydrolysis, and exposure to strong bases (i.e. NaOH or permanganate). These straightforward approaches produce a high, in some cases too high, density of functional groups such as —COOH, —NH, —OH, —CONH, etc. on the fiber surface for either analyte interaction or further modification processing under mild ambient conditions. Unfortunately, these approaches to polymeric solid phase modification are detrimental to the physical structure of the solid material as they can break down the basic polymer/fiber backbone. The well-established approach of plasma grafting to polymer surfaces has also been evaluated as a means to generate tailored surfaces without compromise of phase integrity. For example, a grafting-to approach has been evaluated utilizing polyacrylic acid (PAA) as a means of generating an anionic surface on a polymeric fiber to immobilize transition metal ions from aqueous solution. Unfortunately, the polymeric fiber and column structure provided a challenge in the grafting process, resulting in a non-uniform oxidation and therefore heterogeneous distributions of active sites.

What is needed in the art are improved sorbent media for separation applications that can address these and other problems in the art. For example, what is needed in the art is a more generalized approach to surface modification of a polymeric solid phase while still imparting specificity for the desired solid phase separation technology.

SUMMARY

According to one embodiment, a surface modified solid phase for a chromatography separation protocol is disclosed. More specifically, the surface modified solid phase includes a polymeric solid phase comprising a hydrophobic surface and a lipid. The lipid includes a hydrophobic end and a headgroup opposite the hydrophobic end, the hydrophobic end being adsorbed to the hydrophobic surface of the polymeric solid phase. The headgroup includes a binding functionality that can be used to target an analyte in a separation protocol.

Also disclosed are chromatography separation devices that can include the surface modified solid phase and methods of utilizing the separation devices. For instance, a method can include contacting the surface modified solid phase with a sample. The binding functionality of the headgroup can bind the analyte carried in the sample so as to separate the analyte from the remainder of the sample.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

The same reference characters designate the same or like components throughout the drawings and description.

DETAILED DESCRIPTION OF REPRESENTATIVE EMBODIMENTS

Definitions

Figure 1:
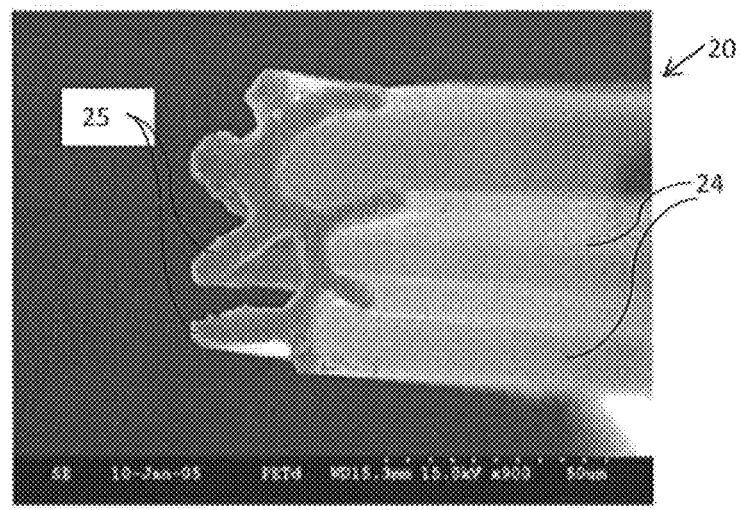
FIG. 1 illustrates one embodiment of a capillary-channeled fiber.

As used herein, the term "liquid chromatography" generally refers to a technique for separation of a mixture by use of a solid material as the stationary phase to affect target molecule capture on the solid stationary phase. The technique can also include a mobile phase that may incorporate any fluid or mixtures of fluids including liquid, gas, or supercritical fluids and may include polar or non-polar solvents. Liquid chromatography methods encompassed herein can include, without limitation, analytical and preparative liquid chromatography, affinity chromatography, solid phase extraction and high performance liquid chromatography including reversed phase, ion-exchange and hydrophobic interaction chromatography modalities, among others.

As used herein, the term "test sample" generally refers to any material suspected of containing an analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, fermentation broths, cell lysates and so forth, are likely materials requiring the selective immobilization capabilities described herein. The test sample may be used directly as obtained from the source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

As used herein, the term "protein" refers to any molecular chain of amino acids that is capable of interacting structurally, enzymatically or otherwise with other proteins, polypeptides or any other organic or inorganic molecule.

As used herein, the term "polypeptide" refers to a molecular chain of amino acids and does not refer to a specific length of the product. Thus, di-peptides, oligopeptides and proteins are included within the definition of polypeptide. This term is also intended to include polypeptides that have been subjected to post-expression modifications such as, for example, glycosylations, acetylations, phosphorylations, and so forth.

As used herein, the term "nucleotide" or "nucleic acid" refers to a molecular chain of deoxyribose nucleic acids (DNA) or ribose nucleic acids (RNA) which also includes natural as well as unnatural or chemically modified nucleic acids or structural analogs such as polypeptide nucleic acids (PNA) and so forth and does not refer to a specific length of the product.

Detailed Description

Reference will now be made in detail to various embodiments of the disclosure, one or more examples of which are illustrated in the accompanying drawings. Each example is provided by way of explanation, not limitation of the disclosed subject matter. In fact, it will be apparent to those skilled in the art that various modifications and variations can be made in the present disclosure without departing from the scope or spirit of the subject matter. For instance, features illustrated or described as part of one embodiment, can be used on another embodiment to yield a still further embodiment. Thus, it is intended that the present disclosure cover such modifications and variations as come within the scope of the appended claims and their equivalents.

In general, the present disclosure is directed to methods and devices that can be utilized in performing liquid chromatography protocols. More specifically, the present disclosure is directed to surface modified polymeric solid phase materials for use in chromatography separation protocols.

Beneficially, the solid phase includes surface modification that can be highly specific for targeted analytes. Methods for forming the surface modified solid phase materials are also disclosed. Methods generally include adsorption of functionalized lipids to the surface of a polymeric solid phase to impart highly specific selectivity to a chromatography protocol. Beneficially, the methods for modification of the polymeric solid phase can be carried out quickly and easily according to a solution-based adsorption process without detrimental effect on the polymeric solid phase.

The surface modified polymeric solid phase can be utilized as a stationary phase in any chromatography process including, without limitation, reversed-phase, liquid chromatography, high performance liquid chromatography, solid phase extraction, gas chromatography, ion exchange chromatography, etc. In addition, the surface modification process can be carried out at any time prior to carrying out a separation protocol. For instance, the solution-based functionalized lipid adsorption process can be performed either prior to or following assembly of a plurality of stationary phase solids in a column format. Following surface modification of the solid phase, the column can be utilized as is or the materials can be further processed. For example, surface modified fibers can be segmented for use in a different system, for instance by attachment to micropipette tips. The surface modification process can be utilized in many different systems, ranging from clinical diagnostics on fiber tips to polymeric fiber columns used in preparative chromatography or analytical chromatography. Beneficially, this methodology could be implemented on virtually any hydrophobic support surface used for species-specific capture.

Several advantages exist for the modification approach described herein. For example, the solid phase structures (e.g., polymeric fibers) can be packed into a column or other device prior to modification therefore ensuring uniform exposure of the solid phase to the functionalized lipid during surface modification, generating a homogenous modification of the stationary solid phase surface. Second, the modification approach can employ chemistries that occur under ambient conditions. Additionally, the wide array of available functionalized lipids presents a rich portfolio of separation mechanisms, and the surface modified solid phase can exhibit high stability upon contact with solvents as are commonly utilized in liquid chromatography separation protocols. Moreover, the modification approach is extremely flexible; virtually any lipid can be absorbable to a hydrophobic polymeric surface of the solid phase generating a modified surface in a single-step application. The ability to change the analyte specific interaction is as easy as a lipid substitution. The only experimental procedure changes that might be required would be specific to the analyte and minimization of nonspecific binding in that situation.

Functionalized lipids as may be utilized to provide the desired specificity to the polymeric solid phase can include a hydrophobic end and a head group that includes the desired functionality to be applied to the polymeric solid phase surface. In one embodiment, a functionalized lipid for use in a surface modification protocol can be a polyethylene glycol modified phospholipid having a general structure of:

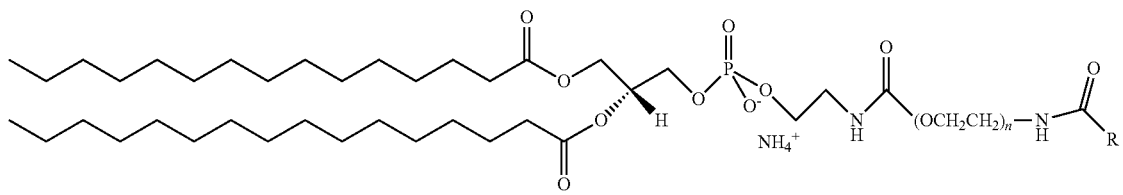

wherein R designates a headgroup that can provide the desired specific functionality to the surface of the polymeric solid phase material and n can generally be between 0 and about 200, or between about 7 and about 113. Of course, the functionalized lipid is not limited to a phospholipid as illustrated above and other functionalized lipids as are generally known in the art may alternatively be utilized. For instance, the functionalized lipid can be a functionalized glycerolipid (e.g., a mono-, di-, or tri-substituted glycerol), a glycerophospholipid, a fatty acid, or any other suitable lipid that includes a hydrophobic end that can adsorb to the surface of the polymeric solid phase and also can be functionalized to include a headgroup that can provide specific binding capability for the polymeric solid phase.

In general, the functionalized lipid can include a hydrophobic end that incorporates one or more saturated or unsaturated aliphatic chains that can be readily adsorbed to the polymeric surface of the solid phase. For instance, the hydrophobic end of the functionalized lipid can have the general structure of:

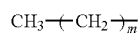

wherein m can be from about 6 to about 30 or from about 14 to about 18.

The headgroup of the functionalized lipid can be designed to provide the desired binding specificity to the solid phase material. In one embodiment, the headgroup can include a functional group R that can bind a biological analyte of interest. For instance, the functional group can include a nucleotide, a coenzyme, a polypeptide, or the like, that can bind a biomolecule such as a proteinaceous biomolecule of interest. Of course, the headgroup is not limited to coenzymes and polypeptides, and any binding agent as is generally known or developed for an analyte of interest can be utilized. For example, the headgroup can include a reactive functionality that can target an analyte of interest. For example, the headgroup may include a terminal carboxyl group, hydroxyl group, a substituted or non-substituted amino group, a nitro group, or the like that can bind a targeted analyte.

Examples of functionalized lipids as may be utilized to modify the surface of a polymeric solid phase material can include, without limitation,

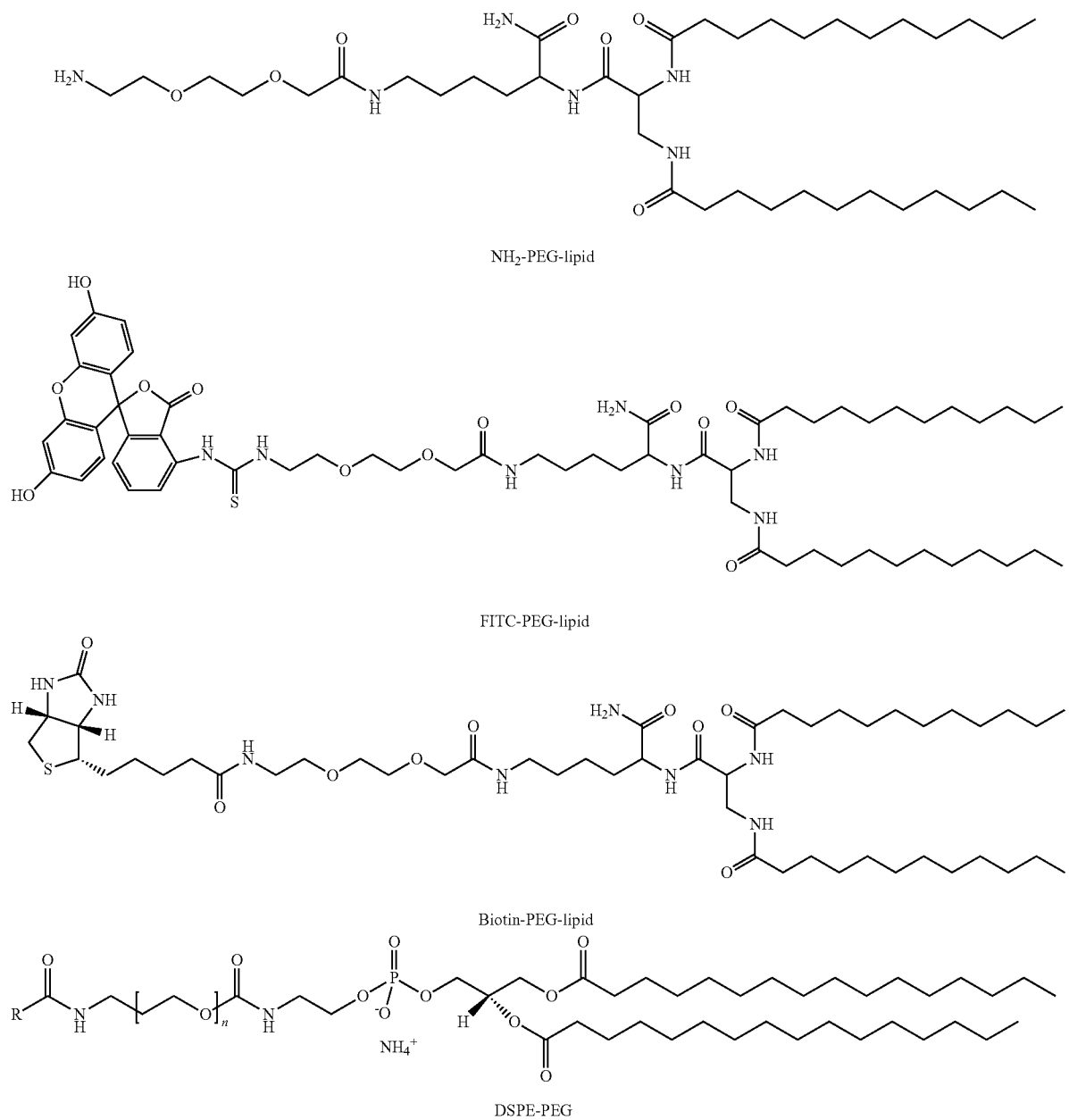

The headgroup can include a specific binding member for the analyte of interest. Specific binding members generally refer to a member of a specific binding pair, i.e., two different molecules where one of the molecules chemically and/or physically binds to the second molecule. For instance, immunoreactive specific binding members can include antigens, haptens, aptamers, antibodies, and complexes thereof, including those formed by recombinant DNA methods or peptide synthesis. An antibody can be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art.

Other common specific binding pairs include but are not limited to, biotin and avidin, lectins and carbohydrates, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte.

The functional headgroup can be bound to the lipid according to any desired methodology. For instance, the functional headgroup can be directly bound to the lipid or can be bound to the lipid by use of a hydrophilic spacer, for instance a poly(ethylene glycol) spacer as in the general structure provided above. Moreover, the length of the spacer can be varied as is known. In addition, the spacer can be utilized to provide desired characteristics to the surface modified solid phase. For instance, the spacer can provide a site for stereo-chemical control of the surface modification. Variation in the length of the spacer can be utilized, for example, to tune the degree of interaction between the functional headgroup and the mobile phase during a separation protocol. Such functionalized lipids have been described previously in biologically based research (see, for example, U.S. Pat. No. 5,395,619 to Zalipsky, et al., U.S. Pat. No. 6,224,903 to Martin, et al., and U.S. Pat. No. 6,605,299 to Zalipsky, all of which are incorporated herein).

A variety of functionalized lipids are available on the retail market. The commercial availability of these functionalized lipids and the wide range of available head groups provide easy access to many potential surface modifications using one basic approach. By way of example, a wide variety of functionalized lipids are available from Avanti® Polar Lipids, Inc. of Alabaster, Ala. By the same token, there are a variety of synthetic methodologies, such as solid phase protein synthesis (SPPS), by which functionalized can be readily generated in the laboratory.

The polymeric solid phase to which the functionalized lipids can be adsorbed to form the surface modified solid phase can generally be of a size and shape so as to be utilized in a chromatography protocol. For instance, the polymeric solid phase can be in the form of polymeric beads or fibers as are generally known in the art.

According to one embodiment, capillary-channeled polymeric fibers can be utilized as the solid phase. As previously stated, capillary-channeled fibers can be beneficial in chromatographic separations as they can provide for high contact area and high linear velocity with low back pressure. For instance, capillary-channeled fibers can provide relatively small interstitial fractions within the column (i.e., the interstitial volume per unit volume of the packed column), for instance about 1.0 or less, about 0.75 or less, or about 0.65 or less in some embodiments and high fiber density such as about 4 mg/cm$^3$ or greater, or about 5 mg/cm$^3$ or greater in some embodiments. Meanwhile, a column of packed capillary-channeled fibers can be operated at a linear velocity of about 25 mm/sec or greater, for instance about 50 mm/sec or greater or about 100 mm/sec in some embodiments, with a back pressure of about 2000 psi or less.

Figure 2:
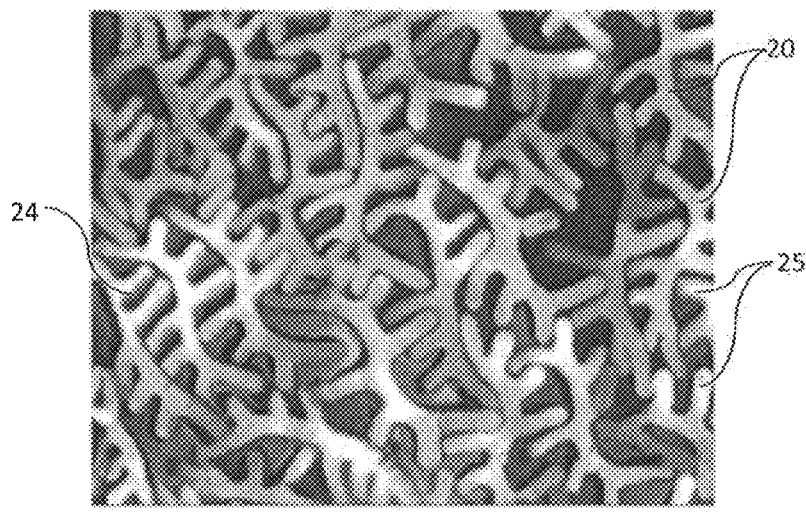
FIG. 2 illustrates a cross sectional view of a plurality of capillary-channeled fibers generally aligned and packed together as in a column.
Figure 3A:
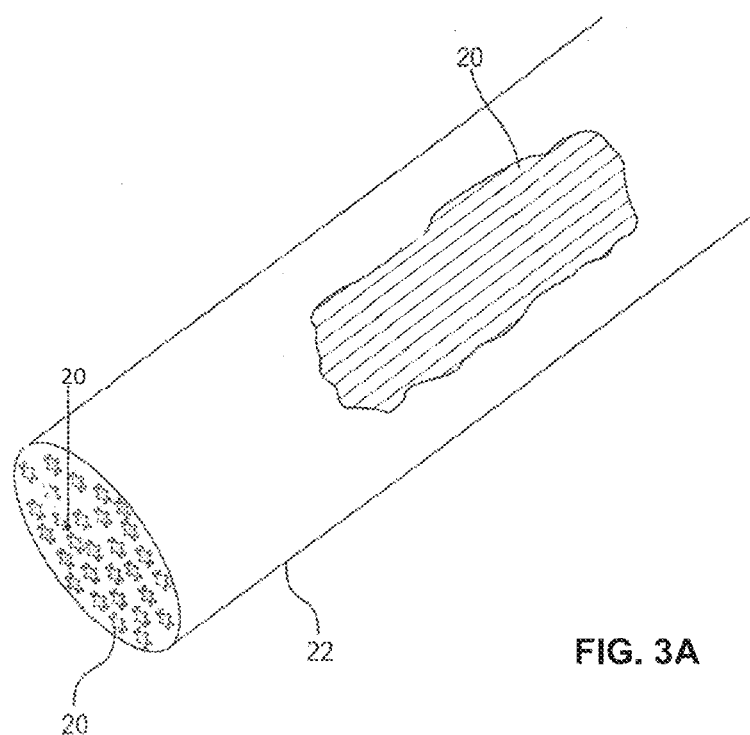
FIG. 3 includes a schematic representation of a perspective view of a conduit packed with a plurality of capillary-channeled polymeric fibers (FIG. 3A) and a scanning electron micrograph (SEM) image of a microbore column packed with a plurality of capillary-channeled polymeric fibers (FIG. 3B).
Figure 3B:
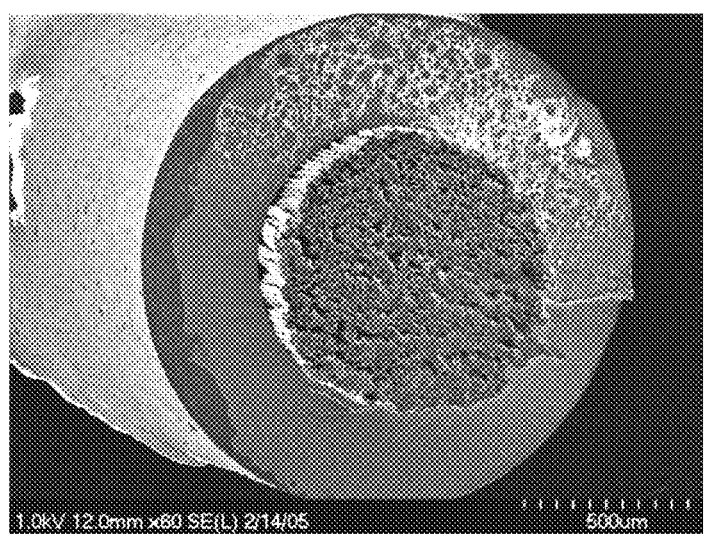
Figure 4:
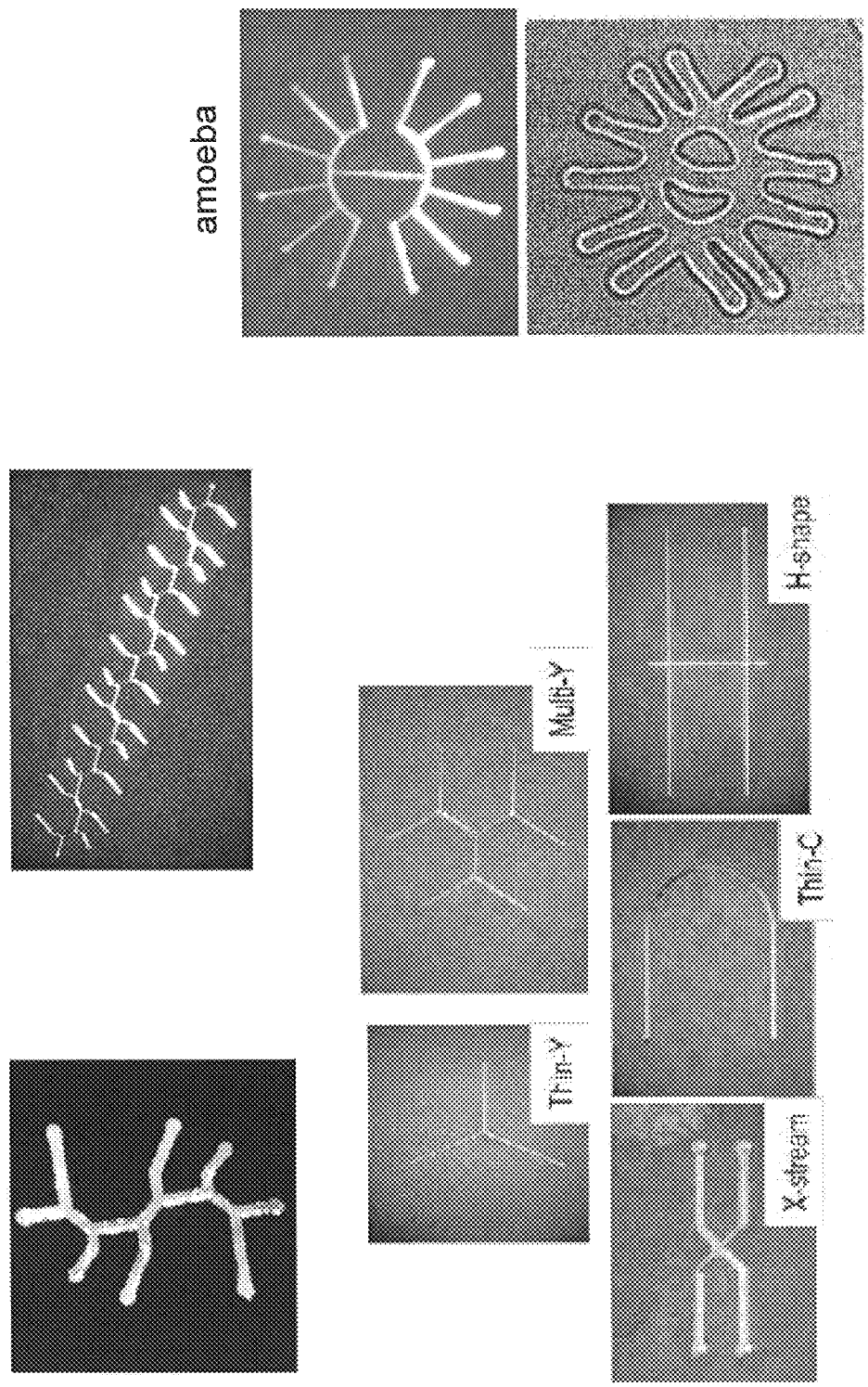
FIG. 4 illustrates several different embodiments of capillary-channeled polymer fibers.

In one embodiment, the capillary-channeled polymeric fibers utilized can be similar to those disclosed in U.S. Pat. Nos. 7,740,763; 7,374,673, and 7,261,813; previously incorporated herein by reference. Referring to FIG. 3A, a perspective view of a plurality of capillary-channeled polymeric fibers 20 are shown packed into a casing 22. FIG. 3B illustrates an SEM of 120 polypropylene capillary-channeled fibers 20 in a drawn fluorinated ethylenepropylene microbore casing 22. As shown in FIGS. 1-3, each fiber strand 20 has a plurality of co-linear capillaries 24 extending the entire length of the exterior surface of the fiber 20. Each capillary 24 is defined by a pair of opposed walls 25 that extend generally and longitudinally and form part of the exterior surface of the fiber 20. Desirably, these capillaries 24 and walls 25 extend down the entire length of the fiber 20 parallel to the longitudinal axis of the fiber 20 and are nominally co-linear on each fiber 20. This produces de facto substantially the same co-linear capillaries 24 along the entire length of the casing 22. It should be understood that the particular shapes of the capillary-channeled fibers illustrated in FIGS. 1-3 are not a requirement of the present disclosure. In particular, the number and/or cross-sectional shape of the capillaries as well as the overall shape of the capillary-channeled fibers can vary from that shown in the figures. For instance, the depth of a single capillary on a fiber, i.e., the radial height of walls 25 on FIG. 1, can range, for instance, between about 1 µm and about 20 µm. FIG. 4 presents several different variants of capillary-channeled polymer fibers as are encompassed herein. The fibers could also be presented in the form of woven/non-woven fabrics and randomly-packed staple material.

In one embodiment, the capillaries 24 can be configured to wrap around the length of the fiber 20 in a helical fashion. In one embodiment, substantially all of the capillaries 24 can be nominally co-linear on each fiber 20. As such, substantially all of the capillaries 24 of a plurality of fibers 20 can follow a helix pattern that has a similar pitch. The pitch is the number of complete turns of a single capillary 24 around the circumference of the fiber 20 per unit of length of the fiber 20. This also can produce de facto substantially the same co-linear capillaries 24 along the entire length of the casing 22.

Additionally, in the course of packing the fibers 20 into a bundle that lays along the entire length of the casing 22, whether the individual fibers have purely linear capillaries 24 or helical ones, it is possible that one or more, even all, of the fibers 20 in the bundle will rotate about its/their own axis or the axis of the casing 22 over the entire length of the column. In other words, the capillary-channeled fibers 20 may twist as they lay within the casing 22. Accordingly, the capillaries 24 and walls 25 also may twist somewhat.

There are many different fabrication approaches and materials that can be utilized to form the solid phase structures, e.g., the capillary-channeled polymeric fibers 20. For instance, the capillary-channeled polymeric fibers 20 are amenable to formation from any polymers that can be melt spun. By way of example, formation of capillary-channeled fibers as may be utilized as described herein has been described in U.S. Pat. No. 5,200,248 to Thompson, et al. and U.S. Pat. No. 5,972,505 to Phillips et al., which are incorporated herein by reference. A non-limiting list of exemplary materials from which the solid phase can be formed can include polyolefins (e.g., polyethylene, polypropylene, polybutylene, etc.), polyesters (e.g., polyethylene terephthalate (PET)), polyanilines, polylactic acid, and polyamides (e.g., nylons), poly(styrene-divinyl benzene), methacrylates, etc., as well as polymer blends and copolymers including random copolymers and block copolymers of any monomeric or oligomeric precursor. In one embodiment, a polymer that exhibits relative chemical inertness and highly hydrophobic surface, for instance a polyolefin such as polypropylene, PET, or nylon-6 can be utilized in forming the solid phase structures. A hydrophobic polymeric material can provide support for the adsorption of the aliphatic tails of the functionalized lipids during the surface modification process.

The solid phase structures can be formed to a suitable size and shape for the desire separation protocol. For example, fibers can be formed to a desired size and shape to promote capillary flow of a liquid with a predetermined viscosity through a casing. For instance, the nominal diameter of a fibrous solid phase structure (e.g., the diameter of the fiber encompassing the surface capillaries in the case of a capillary-channeled fiber) can range from about 10 micrometers to about 80 micrometers (µm), or from about 35 micrometers to about 50 micrometers.

In general, the polymeric solid phase structures can be held in a casing such as illustrated in FIG. 3A and FIG. 3B.

Casing 22 can be of any material compatible with a solid phase separation protocol. For example, casing 22 can be a glass, ceramic, metallic or polymeric material. In one embodiment, casing 22 can be formed of the same or similar polymeric material as is used to form fibers 20. For instance, casing 22 can be formed of the same base polymer as is used to form the capillary-channeled fibers 22, though the finished materials may vary somewhat with regard to additives such as clarifiers, nucleating agents, stabilizing agents, other polymers or polymer components, and the like. According to this embodiment, the inner surface of the casing can also be surface modified with the functionalized lipid, and the available surface area for interaction between the sorbent media and the sample can be even greater, as it can also include the interior contact surface of casing 22.

Figure 5:
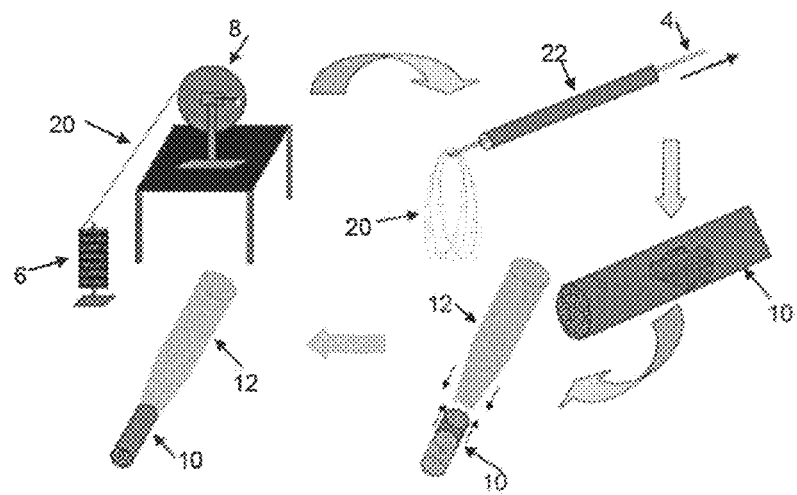
FIG. 5 schematically illustrates a method of forming a device as may incorporate the surface modified polymeric solid phase materials as described herein.

According to one embodiment, casing 22 can form the body of a detachable extraction conduit 10 as is illustrated in FIG. 5. A detachable extraction conduit 10 can be used in large or small volume separation protocols. For instance, extraction conduit 10 can be removably attachable to a micropipette tip for use in a small volume micropipette solid phase extraction protocol. Accordingly, an extraction conduit 10 can be of a cross-sectional shape and size so as to be removably attachable to a micropipette tip. Of course, methods for utilizing the surface modified solid phase structures are not limited to small volume solid phase extraction protocols, and the surface modified polymeric solid phase materials may be utilized in any separation protocol as previously discussed.

An extraction conduit 10 can have an inner diameter suitable for the desired application. For example, the extraction conduit can have an inner diameter from about 0.5 mm to about 5 mm, for instance from about 1 mm to about 3 mm. Of course, an extraction conduit need not be circular in cross section, and can describe any cross sectional geometry. The length of a detachable extraction conduit 10 can generally vary depending upon the particularities of the separation to be carried out including volume of the test sample, flow velocity, analyte affinity for the fibers, etc. For example, when considering small volume separation protocols, i.e., less than about 1 mL in volume, an extraction conduit 10, can generally be between about 0.5 cm and about 3 cm in length. In other embodiments, however, an extraction conduit can be longer, for instance up to about 10 cm in length, or even longer in other embodiments, for example when utilizing a large volume sample.

FIG. 5 illustrates one method for forming and using a detachable extraction conduit 10. According to this particular embodiment, a fibrous solid phase structure, for instance a capillary-channeled fiber 20, can be fed from a fiber spool 6 to a rotary counter 8. A loop of capillary-channeled polymer fiber 20 containing the desired number of wraps can then be removed from the rotary counter 8 and attached to a monofilament 4. The monofilament 4 can be used to pull the loop of capillary-channeled polymer fibers 20 through the casing 22. The casing 22 containing the fibers 20 can then be trimmed as desired to form the detachable extraction conduit 10. Prior to utilization, the fibers can be surface modified to include a functionalized lipid at the fiber surface. For instance, a solution containing the functionalized lipid can be exposed to the fibers, such that the functionalized lipid adsorbs to the surface of the fibers. A functionalized lipid solution can be an aqueous solution such as a water/alcohol solution. By way of example, a 50:50 water:ethanol solution can be formed that includes the functionalized lipid in a concentration of from about 1 to about 10 micrograms per milliliter (μg/mL). To ensure homogeneous fiber modification, the casing containing the fibers and the functionalized lipid solution can be centrifuged. The adsorption method is not critical, however, and the solid phase structures may alternatively be surface modified to include the functionalized lipid prior to location within a casing. Following formation, the extraction conduit 10 can be removably attached to a fluid flow device, for instance a micropipette tip 12 as shown.

During use, an extraction conduit containing the surface functionalized solid phase structures can be utilized according to known practice. For example, an aspirator can be provided to move fluid through a casing to encourage contact between the fluid and the surface modified structures held in the casing. In other embodiments, electro-osmosis, pumps, injectors, or any other suitable hydrodynamic means may be utilized to move fluid through a casing. Alternatively, a fluid may move through a casing via wicking action of the fibers alone, with no additional hydrodynamic means utilized in the process.

In one embodiment, a system including the surface modified polymeric solid phase material can be utilized in small volume separation protocols, for instance utilizing a fluid sample of about 1 milliliter (mL) in volume or less. In other embodiments, however, the methods and devices disclosed herein can be utilized for extraction of an analyte from larger samples, for instance, about 1 mL or greater, about 5 mL in volume or greater, or larger samples in other embodiments, such as about 10 mL or greater in volume, or larger yet in other embodiments. Representative devices can, for example, include a casing packed with the surface modified solid phase sorbent media to form an extraction conduit that can be removably attached to a fluid flow system, for instance a system including an aspirator, a pump, or the like. Alternatively, a gravity fed flow can be utilized, optionally in conjunction with centrifugation.

In one particular embodiment, the disclosed devices and methods can be utilized to separate polypeptides from each other and/or from other compounds found in a test sample, for instance compounds found in buffer solutions such as salts, other organics, urea, and detergents. The methods are not limited to this particular embodiment, however, and other separation protocols can also be carried out with the surface modified solid phase media including, for instance, isolation and/or concentration of analyte species such as metal ions as may be found in nuclear waste media as well as extraction of pollutants from water samples. Macromolecular analytes can be targeted by the surface modified solid phase for separation from a fluid mixture in one embodiment. Macromolecular separations have proven difficult with solid phase separation protocols in the past, as many previously existing protocols relied on size differentiation for, e.g., sequestration of the targeted analyte in pores of the solid phase, which is not successful for macromolecular analytes. The chemical separations capable by use of the disclosed surface modified solid phase can be highly successful when targeting macromolecular analytes such as proteins and other polypeptides.

Following adsorption of the target analyte to the surface modified solid phase, the analyte can be recovered via elution with any suitable, compatible solution to which the analyte has a higher affinity as compared to the fiber surface. Isolation and concentration of the analyte can greatly improve sensitivity of detection of the analyte, for instance via mass spectrometry methods including electrospray ionization (ESI-MS) methods and matrix-assisted laser desorption-ionization (MALDI) methods. However, recovery of the analyte from the solid phase is not required, and in some embodiments, it may be preferred to determine the presence or absence of the analyte via examination of the solid phase itself, without recovery of the analyte for separate examination.

The present disclosure may be further understood with reference to the following Examples.

Example 1

Chemicals and Reagents

Polyethylene glycol lipids (PEG) modified to contain either a biotin (1,2-Dimyristoyl-sy-Glycerol-3-phosphoethanolam ine-N-[biotinyl (polyethylene glycol)-2000]) or a methoxy (1,2-Dimyristoyl-sy-Glycerol-3-phosphoethanolamine-N-[methoxy (polyethylene glycol)-2000]) head group (PEG-Biotin and PEG-0Me), were purchased from AVANT® Polar Lipids (Alabaster, AL).

PE-DTPA (1,2-dimyristoyl-snglycero- 3-phosphoethanolamine-N -diethylenetriaminepentaacetic acid) pre-coordinated with $Cu^{2+}$ was purchased from AVANTI® Polar Lipids.

Working solutions of 5 µg/mL of each lipid were prepared in a 50:50 ethanol:water solution. Ethanol was obtained from Fisher Scientific (Pittsburgh, PA) and MILLIQ® water (18.2 MΩ/cm) was derived from a NANOpure Diamond Barnstead/Thermolyne Water System (Dubuque, IA).

Bovine serum albumin (BSA) was obtained from Sigma Aldrich (Milwaukee, Wis.) and prepared to a working concentration of 5 µg/mL in phosphate buffered saline (PBS) consisting of 140 mM NaCl, 10 mM $Na_2HPO_4$, 1.8 mM $KH_2PO_4$, and 2.7 mM KCl at pH 7.3 (Sigma Aldrich, Milwaukee, Wis.).

Two fluorescent proteins (5 µg/mL) were utilized for detection. Streptavidin labeled with Texas Red (SAv-TR) and enhanced green fluorescent protein with a hexahistidine-tag (his-tag EGFP) were employed as the capture species on polypropylene capillary-channeled fiber surfaces modified with PEG-Biotin and PE-DTPA respectively. mCitrine (as TEM8-mCIT) purified and in clarified cell lysate was used to assess non-specific binding.

Modification studies utilizing the affinity of SAv-TR protein solutions for biotin were prepared in a PBS solution. Experiments performed to reduce nonspecific binding to the capillary-channeled polymer fiber surface utilized a SAv-TR protein solution in 0.1% Tween-20 (Rockland-inc.com, Gilbertsville, Pa.) PBS (PBST) solution. Modification studies utilizing the PE-DTPA employed a his-tagged GFP prepared in a 20 mM Tris-HCl buffer (Teknova, Hollister, Calif.). Experiments performed to illustrate non-specific bonding of TEM8-mCit and selective capture of SAv-TR to the biotin-PEG-lipid fiber surface utilized protein concentrations of 0.4 µg/mL (about 14 nM) in PBST or in the lysate.

Capillary-Channeled Polymer Fiber Tip Preparation

A total of 658 polypropylene capillary-channeled fibers were packed to extend entirely through a 300 mm long, 0.8 mm i.d. fluorinated ethylenepropylene (FEP) capillary tube (Cole Palmer, Vernon Hills, Ill.), referred to here as the fiber column. Following cleaning and rinsing of the fibers from any latent spin finish from the extraction process with a range of polar and non-polar solvents by use of an HPLC pump, the column was cut into 1 cm lengths with an additional 6 mm gap at one end. This gap allowed the tubing to be press-fit on to the end of a commercial low-retention micropipette tip (Redi-tip, Fisher Scientific, Pittsburgh, Pa.). Polypropylene capillary-channeled fiber tips of these geometries with no surface modification as described herein have been shown to have binding capacities on the order of 1.5 µg for a range of proteins.

Fiber Functionalizatlion

The fiber tips packed with the polypropylene capillary-channeled fibers were functionalized through a basic adsorption process, utilizing the affinity of the aliphatic lipid side chains for the hydrophobic polypropylene surface. The lipid solutions (PEG-Biotin, PEG-OMe, and PE-DTPA) were prepared to working concentrations in a 50% water:ethanol solvent, balancing their solubility with the tendency for surface adsorption. The lipid solutions were exposed to the fiber tips in 1 mL aliquots and centrifuged (Clinical 50, VWR, West Chester, Pa.) at 1200 relative centrifugal force (RCF) for 3 minutes. This approach allowed for the solvents to pass uniformly through the fiber interstices so that surface modification could occur homogenously. As noted above, chemical modification of complete fiber columns would increase the experimental throughput.

Experimental Outline

Each experiment utilized three different fiber columns: an analyte specific column (modified with biotin-PEG-lipid), a control column (modified with OMe-PEG-lipid) and a bare polypropylene column. The functionalized columns were washed with PBS or PBST, depending on the experiment and then a BSA block was applied. In each case, 1 mL solutions were passed through the tips as described above. The BSA block ensured that the analyte protein exposed to the surface during the experiment did not adsorb itself to the bare polypropylene due to non-specific hydrophobic interactions. After a buffer wash the fibers were exposed to the fluorescently labeled protein test solutions. Finally, all tips were washed with buffer prior to imaging to remove residual, nonspecifically bound, fluorescent protein from the fiber tips.

Images and Statistical Data

The capillary-channeled polymer fiber packed tips were removed from the commercial micropipette tip and taped onto a glass microscope slide. Fluorescent images of the fiber tips were generated on an Olympus IX71, 4×/0.13 UPlanFI (infinity corrected) objective (Olympus, Center Valley, Pa.). Fluorescent excitation was achieved using a Xe arc lamp with spectrophotometer filters (Chroma, Bellows Falls, Vt.) set at excitation 575/25 and emission 624/40 for SAv-TR or excitation 494/20 and 531/22 for EGFP. An Ocra-ER (Hamamatsu) CCD camera was used for detection, images were processed and statistical data extracted using SLIDEBOOK™ 5.0 (Denver, Co).

Quantification of Protein Binding

After modification with PEG-lipid, the load and wash solutions that had passed through the fiber tips were each collected individually. The amount of protein bound to the fiber surfaces was determined through fluorescence measurements of the test solutions before and after passage through the tips. Response functions were generated to determine concentration. A Tecan Genio® fluorescence microplate reader (Tecan US, Inc. Durham, N.C.) utilizing a Nune® brand (Sigma Aldrich) black polystyrene 96-well microplate was used for measurement. The relative amounts of protein adsorbed to the fiber surface were determined by subtracting the concentration observed in the solution exposed to the fiber surface from the concentration of the initial load solution. Any protein concentration in the wash was further subtracted from this number to give the final amount of analyte on the surface.

Results

The capillary-channeled fiber packed tips were evaluated for their ability to be functionalized utilizing the strong hydrophobic interaction of the lipid tails with the aliphatic structure of the polypropylene surface. While not wishing to be bound by any particular theory, it was believed that the lipid tail would lay along the fiber surface while the functionalized head group would remain in free solution, allowing for analyte interaction. However, the hydrophobic tails could also intercollate into the polymer fiber phase. Initial proof of concept was demonstrated utilizing the well understood interaction and high affinity of biotin and SAv. Use of the TR-modified SAv allows easy fluorescent imaging of immobilized protein on the fiber surface and quantification of solution composition.

Figure 6:
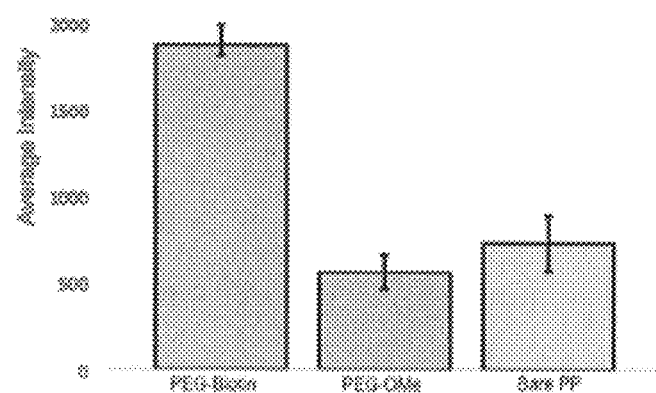
FIG. 6 graphically illustrates the binding of an analyte to solid phase materials as described herein.

FIG. 6 graphically depicts the average intensity response for columns for triplicate experiments, which was collected from an identical size mask down the center of fluorescent images of the fiber-packed columns. As can be seen, there are pronounced differences in the intensities of the fluorescence. A statistically-significant difference between the columns modified with biotin-PEG-lipid and the two control columns analyzed is seen. The two control columns are not significantly different, but the trend that the BSA-treated PP surface affects more non-specific binding suggests that hydrophobic and ionic interactions play a role. The amount of BSA exposed to the surfaces was about 200 times the expected binding capacity of a 1 cm non-surface modified polypropylene capillary-channeled packed fiber tip, sufficient to coat the fiber surface. Therefore, protein-protein interactions between the SAv capture protein and the BSA already on the surface of the fibers is suggested here. Given there was a directional aspect to the initial PEG deposition, as well as to the loading of the target analytes, there was a natural question as to the homogeneity of the overall processes as a function of distance down the fiber tips. The uniformity of the capture process across the entire 1 cm tips was quite high, with a spatial variability of less than 10%, relative.

Figure 7:
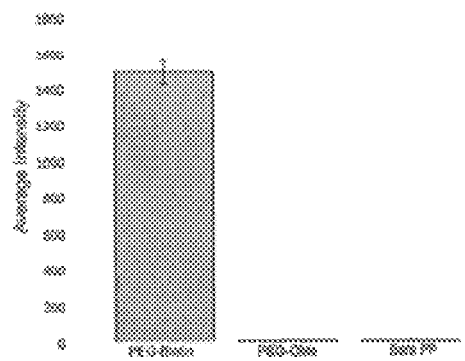
FIG. 7 graphically illustrates the binding of an analyte to solid phase materials as described herein.

In order to evaluate if a significant portion of the non-specific binding was a result of hydrophobic interaction or the protein-protein interactions between the SAv-TR and the BSA-coated fibers, the experiment was repeated substituting the BSA block with a surfactant wash. In this experiment a 0.1% Tween-20 in PBS (PBST) buffer was used to prepare the fiber surface after lipid loading. Additionally the SAv-TR capture protein was loaded on the lipid-modified fibers in the PBST buffer. The application of Tween-20 as a blocking agent is common practice in immunoassays and as depicted in FIG. 7 (showing the average intensity response for each column collected from an identical size mask down the center of each fluorescent image) was successful at inhibiting non-specific binding of the SAv-TR with the OMe-PEG and bare polypropylene surfaces of capillary-channeled fibers. Tween-20 completely prevented nonspecific binding from occurring on the fiber surface while allowing uniform coverage of the SAv-TR with the PEG-Biotin coated fibers.

The second demonstration of functionalized lipids for fiber surface modification utilized DPTA-PE to affect an IMAC-type interaction. IMAC is one of the most powerful approaches in the process-scale purification of proteins from *E. coli* mixtures. When utilized in this fashion the proteins targeted for extraction have been expressed with a poly-histidine tag (his-tag). The high density of histidines, usually hexa his-tags, promotes transition metal coordination. Since the DTPA-PE is pre-chelated with $Cu^{2+}$, the stationary phase is prepared for application in IMAC is a single straightforward step. In this case, $Cu^{2+}$ coordinated with the deprotonated acetic acid groups on the DPTA is available for protein capture via the his-tags. The IMAC-type experiments were performed utilizing a his-tagged green fluorescent protein (GFP), a naturally fluorescent protein. The same experimental steps as applied previously were employed: a buffer wash of the capillary-channeled polymeric fiber tips, a BSA block, and exposure to 5 μg/mL GFP in 20 mM Tris-HCl. The resulting images showed very high levels of non-specific binding in the two control (OMe-PEG and BSA-PP) tips. Potential contributions from the FEP tubing at this combination of excitation/emission wavelengths was ruled out by removing the fibers and illuminating the tubing alone, wherein there was no indication that any spectroscopically-active components were present. The inability to distinguish between the controls and the modified C—CP fibers means the experimental conditions under which the his-tag proteins are exposed to the fibers surfaces allows for a large amount of non-specific binding.

Protein-protein interactions, hydrophobic interactions with support surfaces or the BSA coatings, electrostatic interactions, and interactions between other amino acid residues in the protein (not the his-tag) and the chelating head group are all potential sources of non-specific binding across the spectrum of immobilization-based separations and diagnostics. Additionally, it is possible that the his-tag portion of the protein wasn't capable of binding to the DTPA-PE, i.e., it was not accessible. Different from the case of the biotin-PEG system, this lipid lacks the polyglycol functionality, so it is possible that the chelating head group is too close to the fiber surface to allow for efficient interaction. A final possibility is the fact that while the intended chelation interactions do occur at the PE-DPTA surface, non-specific retention on the control surfaces is just as prevalent. Thus, the simple rinse step (1 mL of 20 mM Tris-HCl) was ineffective at removing non-specifically bound protein. A wide range of experimental variables were evaluated, including lipid loading conditions, BSA blocking, exposure conditions for GFP, various concentrations of lipids and proteins, none of which yielded the desired immobilization performance.

Figure 8:
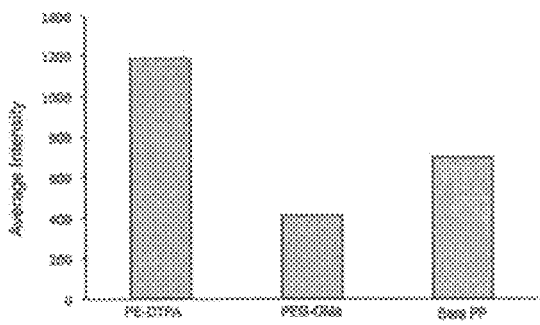
FIG. 8 graphically illustrates the binding of an analyte to solid phase materials as described herein.
Figure 9:
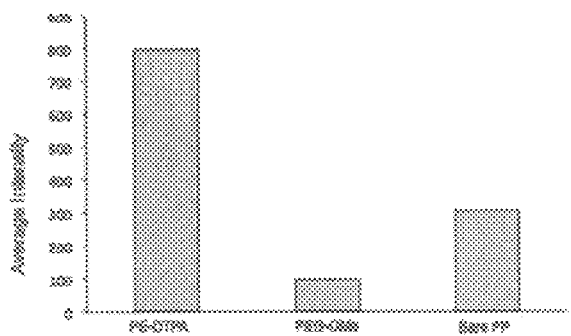
FIG. 9 graphically illustrates the binding of an analyte to solid phase materials as described herein.

Two sets of experimental conditions did result in successful modification with a significant response relative to the controls utilized. FIG. 8 depicts the graphical results obtained from fluorescent images of the PE-DTPA $Cu^{2+}$-chelated, PEG-OMe, and the plain polypropylene fibers that were exposed to the his-tag GFP, with the variation of using a 1 M NaCl wash. For the surface modified fibers, the polypropylene capillary-channeled fibers were exposed to the lipid, the BSA block applied, and then GFP exposure under the same set of experimental conditions as previously described. The NaCl wash presented a relatively high ionic strength environment in the mobile phase, thereby decreasing the propensity for electrostatic interactions on the control surfaces. Clearly the 1M salt wash decreased the relative extent of nonspecific binding, but as evident in FIG. 8, a relatively high level still occurred. The second successful approach to reducing nonspecific binding involved the loading of the GFP protein in the presence of 20 mM Tris buffer that contained 20 mM of imidazole. This particular situation would be expected to decrease nonspecific interactions, and is a common practice on commercial IMAC columns. Taken a step further, an alternative washing step using the same buffer combination of 20 mM Tris and 75 mM imidazole was evaluated to decrease the amount of non-specific binding in each of the fiber/ligand systems. Clearly depicted in the graphical results of FIG. 9, residual non-specific binding to the control surfaces has been all but totally eliminated. As seen, the use of the imidazole rinse reduced the amount of binding in the case of the IMAC chelate by ~30% relative to what was seen in FIG. 8, which likely reflects nonspecific binding, in general, or perhaps reflects an overloading of the stationary phase. At the same time, the integrated intensities for the OMe-PEG and BSA-PP controls were reduced by about 80% and about 60%, respectively. Taken a step farther, it was seen in the fluorescent images that the background fluorescence levels originate from anomalous "hotspots", and are not distributed homogeneously as seen in images in other samples. In fact, these artifacts were also seen in the fluorescent images utilized to develop the graph of FIG. 8. These intense regions, existing at the entrance end of the tips, are likely the result of underivatized polypropylene base fibers or particulate matter from the test solutions captured at the fiber heads.

Figure 10A:
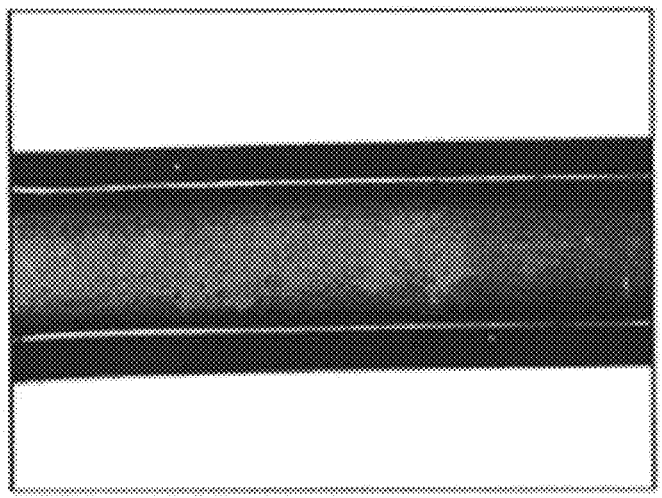
FIG. 10A is a fluorescent image of a biotin-PEG-lipid modified polypropylene capillary-channeled fiber following exposure to a lysate spiked with a streptavidin-containing analyte.
Figure 10B:
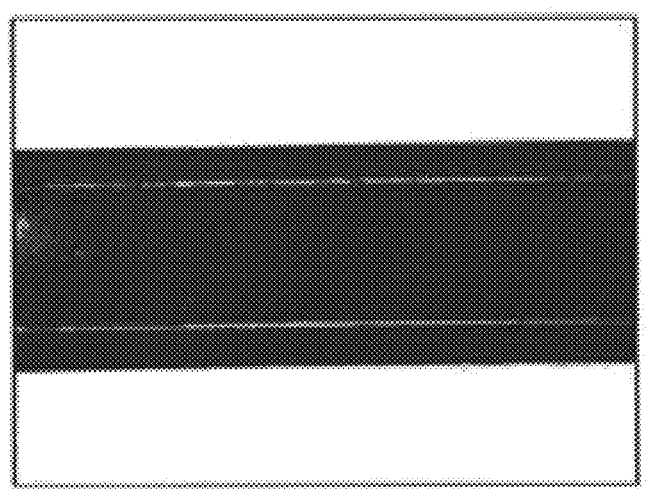
FIG. 10B is a fluorescent image of a native, unmodified polypropylene capillary-channeled polymer fiber following exposure to the same lysate as in FIG. 10A.
Figure 10C:
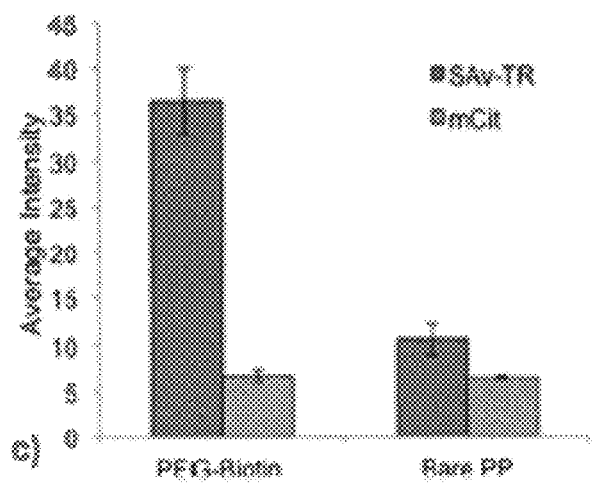
FIG. 10C graphically presents the average fluorescent responses for biotin-PEG-lipid and untreated (bare) polypropylene capillary-channeled polymer fiber columns to the same lysate, the responses were collected from an identical size mask down the center of each column.

To illustrate the ability of biotin-PEG modified capillary-channeled fibers to capture SAv-TR from a complex lysate and to evaluate possible non-specific capture of other proteins, the capture of SAv-TR out of TEM8-mCit lysate was evaluated. mCit is a variant of yellow fluorescent protein, and is used in this case as a tag for production of TEM8 in *E. coli*. mCit fluorescence from the fiber surface was used as an indication of non-specific protein binding in a practical system. In comparison to proteins in the PBST buffer, a cell lysate contains host-cell proteins and other debris and is also more viscous, leading to the possibility of clogging stationary phases and high back pressures. However, the same volume of cell lysate required only 1 minute more of centrifugation time to pass through modified fiber tips than did analyte buffer solutions, clearly reflecting the advantageous fluid flow properties of capillary-channeled fibers. Fiber tips treated with biotin-PEG-lipid and bare fibers were loaded with TEM8-mCit lysate spiked with SAv-TR to make a 0.4 mg mL$^{-1}$ solution. A lower concentration of SAv-TR was chosen than used in previous experiments (12.5-fold less) with the goal of reducing the concentrations to reflect the same order of magnitude as the competing TEM8-mCit. The lysate His buffer included 0.1% Tween-20, so no BSA-blocking modification step was needed for prevention of non-specific binding. Images were collected with SAv/TR and TEM8-mCit excitation/emission simultaneously, so if both proteins were present, both green and red fluorescence would result. As shown in FIG. 10A, while the SAv-TR signal was evident on the biotin-PEG-lipid fiber tip, there was no visible TEM8-mCit fluorescence. The native, unmodified fiber showed no visible signal from either protein (FIG. 10B). The results of the imaging experiments are graphically presented graphically in FIG. 10C. It was noted that absolute values for non-specific fluorescence observed were similar to those observed in FIG. 7. These data demonstrate that specificity was imparted by the biotin-PEG-lipid fiber coating.

In order to determine the actual amount of SAv-TR and TEM8-mCit binding, fluorescence measurements were performed on the pass-through lysate solutions. Unfortunately, due to the imidazole present in the TEM8-mCit lysate, measurements of SAv-TR were complicated by imidazole fluorescing in the SAv-TR spectral window. Therefore, the relative retention of the two proteins was determined from a mixture of the purified TEM8-mCit and SAv-TR in PBST buffer. The table below shows the quantitative amount of SAv-TR and TEM8-mCit in the load mixtures before and after passage through the biotin-PEG modified and bare PP C—CP fiber tips.

| Solution | SAv-TR (µg) | TEM8-mCit (µg) |
|---|---|---|
| SAv-TR/TEM8-mCit mixture (pre-loading) | 0.26 ± 0.06 | 0.37 ± 0.01 |
| PEG-biotin tip flow-through | 0.08 ± 0.02 | 0.35 ± 0.01 |
| Bare polypropylene tip flow-through | 0.27 ± 0.01 | 0.38 ± 0.01 |

These data indicate that only SAv-TR is binding to the fiber tips, and that about 70% of the applied SAv is captured on the biotin-PEG-lipid surfaces. Non-specific binding was not evident for TEM8-mCit on either bare or biotin-PEG-lipid fiber tips under these conditions. Clearly, the addition of the Tween-20 in the sample matrix inhibited non-specific binding, even in the case of the highly hydrophobic polypropylene surface, eliminating the need for a BSA blocking layer.

Example 2

Fluorescein (FITC) was utilized as the functional head-group of the PEG-lipid. In this way, the loading of the lipid onto the PP fiber surface could be fluorescently imaged. Also evaluated was the chemical robustness of the PEG-lipid surface modification by exposure to several common chromatography solvents. Fluorescence imaging before and after solvent exposure revealed a highly robust surface modification.

Materials

PEG-lipid functionalized to contain a fluorescein head group (1,2-distearoyl-sn-glycero-3-phosphoethanolamine-N-[poly(ethylene glycol)5000-N'-fluorescein) (FITC-PEG-lipid) was purchased from Nanocs Inc. (New York, N.Y.) and prepared to necessary concentrations in 50:50 ethanol:water solution. HPLC-grade ACN, methanol, and ethanol were purchased from EMD Millipore (Darmstadt, Germany). Hexanes were purchased from Fisher Scientific (Pittsburgh, Pa.). MILLIQ® water (18.2 MΩ-cm) was derived from a Millipore water system (Billerica, Mass.) and used to prepare all aqueous solutions. Phosphate buffered saline (PBS) was prepared as 140 mM NaCl, 10 mM Na$_2$HPO$_4$, 1.8 mM KH$_2$PO$_4$, and 2.7 mM KCl at pH 7.4 (Sigma Aldrich, Milwaukee, Wis.). Along with the above-mentioned solutions, 0.1% Tween-20, 5% sodium dodecyl sulfate (Sigma Aldrich), 75 mM imizazole (Alfa Aesar, Ward Hill, Mass.) and 20 mM Tris-HCl (Teknova, Hollister, Calif.) were used as test solutions to test the surface stability of FITC-PEG-lipid modified capillary-channeled polymer fibers.

Fiber Column and Instrumentation

Columns were prepared in two separate forms. For adsorption and breakthrough capacity studies, 100 mm×0.8 mm i.d. PEEK was used as column tubing (Cole Parmer). The column was packed to yield an interstitial volume of $\epsilon_i$≈0.64 (based on uracil retention). The weight of capillary-channeled polymer fiber stationary phase per 100 mm was 17.5±0.2 mg. For examining the stability of the modified surface, 0.8 mm i.d. fluorinated ethylene propylene (FEP) was used as column tubing (Cole Parmer, Vernon Hills, Ill.). For the tip experiments, the column was cut into 1 cm segments with a ~4 mm section of empty tubing left at one end allowing the FEP tubing to be press-fit on to the end of a 1000 µL low-retention pipette tip (Molecular BioProducts, Fisher Scientific, Waltham, Mass.). Solution exposure to tips occurred through centrifugation spin-down (Clinical 50, VWR, West Chester, Pa.) at 1900 relative centrifugal force (RCF). Fluorescent images of modified fiber tips were taken on an Olympus IX71, 2×/0.08 UPlanFI (infinity corrected) objective (Olympus, Center Valley, Pa.) with an excitation of 494 nm and emission of 535 nm, achieved with appropriate filters (Chroma, Bellow Falls, Vt.). An Ocra-ER (Hamamatsu) CCD camera was used for detection. SLIDE-BOOK® 5.0 (Denver, Colo.) was used to process images and produce statistical data. Chromatography experiments were performed on an HPLC system consisting of a Waters (Milford, Mass., USA) Model 600S controller, a Waters Model 600 HPLC pump connected to a Rheodyne 7725i six-port injector valve (Rohnert Park, Calif., USA) fit with a 300 μL stainless steel injection loop, and a Waters Model 2487 dual wavelength absorbance detector at 230 nm. Chromatograms were collected using the Waters Empower 2 data acquisition system and processed with Microsoft Excel (Seattle, Wash., USA). All presented data are representative of triplicate injections.

Dynamic Binding Capacity and Adsorption Isotherm

The dynamic binding capacity (DBC) for FITC-PEG-lipid on the polypropylene capillary-channeled polymer fibers was determined through frontal analysis of breakthrough curves on a 100 mm×0.8 mm i.d. column. Throughout the course of DBC experiments, one single column was used. First, the column was conditioned with ~20 column volumes (CVs) of 50:50 ethanol:water. FITC-PEG-lipid solution was introduced to the column until the concentration in the effluent (C) equaled the concentration of the load solution ($C_o$), based on previous injections performed with no column. Adsorbed FITC-PEG-lipid was eluted with 100% ACN until a steady baseline was observed. Finally, the column was equilibrated with ~20 CVs of 50:50 ethanol:water before the next injection. Breakthrough curves were generated at 6 different linear velocities ($U_o$): 8.6, 17.1, 25.7, 34.2, 42.8, and 57.1 mm/s and 7 different concentrations (0.005, 0.05, 0.25, 0.5, 1, 2, and 3 mg/mL). The amount of adsorbed FITC-PEG-lipid was calculated at 50% breakthrough (when $C/C_o=0.50$) using the following equation:

$$q=C_o(V_b-V_{dead})/W$$

where
q represents the binding capacity (mg PEG-lipid/g stationary phase), $V_b$ is the effluent volume at 50% breakthough (mL),
$V_{dead}$ is the dead volume of the system (mL),
$C_o$ is the load concentration of PEG-lipid (mg/mL), and
W is the dry mass of the fibers in the column (g).

The loading capacity was reported as an average of triplicate injections.

Evaluating the Stability of the PEG-Lipid Modification

Solutions were centrifuged through polypropylene capillary-channeled fiber 1 cm tips in 1 mL aliquots for 3 minutes. Tips were first conditioned with 50:50 ethanol:water, then loaded with 5 μg/mL FITC-PEG-lipid. After a wash with 50:50 ethanol:water to remove any un-adsorbed lipid, three tips were exposed to 3 mL of each test solution. A final wash with 50:50 ethanol:water was necessary for comparable fluorescence in the same pH yield comparable fluorescence intensity across all samples due to FITC's pH dependence. Fluorescent images were taken before and after exposure to the test solutions and mean intensities were recorded.

Results and Discussion
Dynamic Binding Capacity and Adsorption Isotherm

Figure 11:
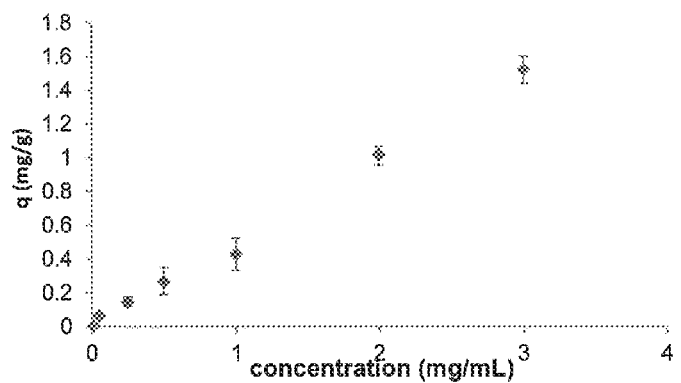
FIG. 11 graphically illustrates the dynamic binding capacity for solid phase materials at several different FITC-PEG-lipid concentrations.

Breakthrough curve analysis was performed on the 100 mm×0.8 mm i.d. column. Breakthrough curves were obtained from injections at 1 mL min$^{-1}$ with 0.005 to 3 mg mL$^{-1}$ FITC-PEG-lipid. The DBC was calculated at each concentration and the resulting adsorption isotherm is shown in FIG. 11. The isotherm was generated at the highest flow rate used, as capillary-channeled polymer fibers have consistently shown enhanced performance at higher flow rates due to their enhanced mass transfer ability and low back-pressures. The data clearly remain linear at this concentration range. The isotherm data was fit to a linear isotherm, as well as the common non-linear Langmuir and Freundlich isotherms using Matlab. All three gave similar $R^2$ values with 0.9957 for linear, 0.9952 for Freundlich, and 0.9948 for Langmuir. While this may be due to the "low" concentrations and small range, 3 mg mL$^{-1}$ lipid concentration is considered high, given that the critical micelle concentration, or the minimum concentration necessary for micelles to form, is cited at between 0.03 and 0.07 mg mL$^{-1}$. Remaining linear at this range again highlights the rapid mass transfer ability of the capillary-channeled polymer fibers. The maximum DBC was 1.52 mg of FITC-PEG-lipid per gram of fiber when loading 3 mg g$^{-1}$ FITC-PEG-lipid.

Figure 12:
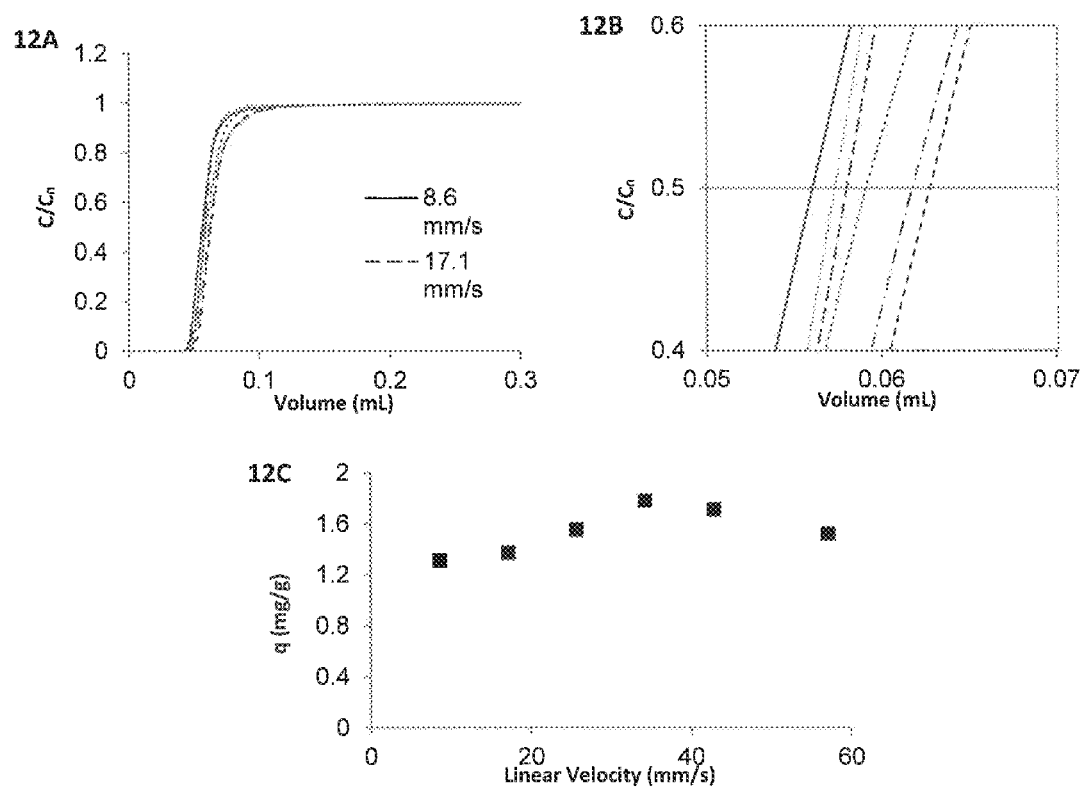
FIG. 12 illustrates the effect of linear velocity on surface modification binding capacity and includes a breakthrough curve at 3 mg/mL flow rate (FIG. 12A), a magnified view of a portion of the breakthrough curve of FIG. 12A (FIG. 12B) and the change in dynamic binding capacity with linear velocity (FIG. 12C).

To evaluate the effect of linear velocity on FITC-PEG-lipid binding capacity, flow rate was varied from 0.15-1 mL min$^{-1}$ (linear velocity $U_o$=8.6-57.1 mm s$^{-1}$). FIG. 12A shows the full breakthrough curves for 3 mg mL$^{-1}$ FITC-PEG-lipid on the PP C—CP fiber column. The shape of these breakthrough curves did not vary significantly between flow rates; FIG. 12B gives a magnified view at 0.5 C/$C_o$ where DBC was calculated. The difference in volume of breakthrough between flow rates is also very small. With little kinetic limitations, it is expected that breakthrough curves in volume terms should be the same, and that is observed here. As seen in FIG. 12C, DBC initially increases from 0.15 to 0.6 mL min$^{-1}$ and then decreases as flow rate is increased past 0.6 mL min$^{-1}$, giving an optimal flow rate of 0.6 mL min$^{-1}$.

The maximum binding capacity was found at 0.6 mL min$^{-1}$ to be 1.78 mg of FITC-PEG-lipid per gram of fiber, or 0.38 μmol/mL fiber. There are several factors that may explain this including the way the PEG-lipid is adsorbing to the fiber surface, or that maximum capacity of the fiber column has not actually been reached. However, the advantages of capillary-channeled fibers can still stand out, with high throughput and low cost advantages leading to more efficient separations that can purify more product in a smaller amount of time and at a lower cost.

Stability of FITC-PEG-Lipid on Polypropylene Capillary-Channeled Fibers

Figure 13:
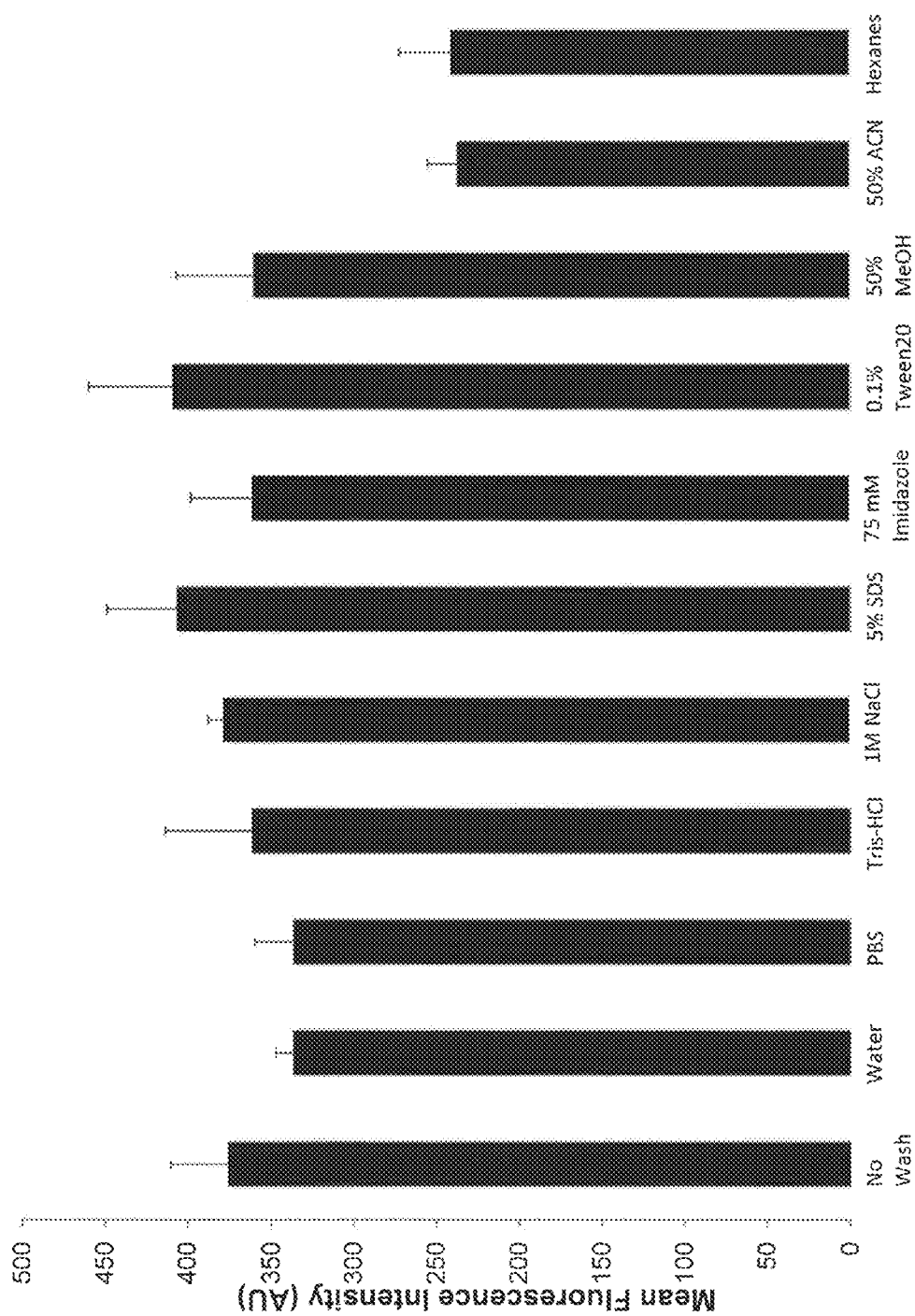
FIG. 13 illustrates the intensity of fluorescence for FITC-PEG-lipid surface modified solid phase materials following exposure to several different solvents.
Figure 14:
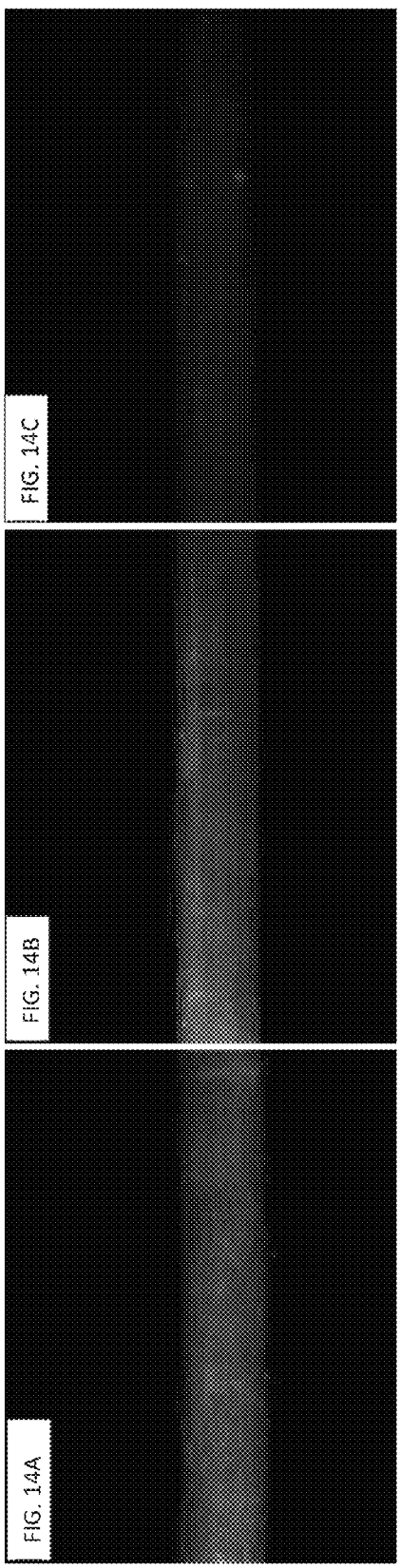
FIG. 14 presents three images (FIG. 14A, FIG. 14B, FIG. 14C) of three surface modified fibers following exposure to a targeted analyte and different solvents.

The extent of the interaction between the lipid tail and the polypropylene surface of the fibers was evaluated as modification occurred through adsorption to the fiber surface. This evaluation was done through fluorescent imaging of FITC-PEG-lipid modified fibers. The imaging was done on-column with fibers packed into FEP tubing and cut to 1 cm. FIG. 13 shows the mean intensity of FITC fluorescence after exposure to the solvents listed. As fluorescein has pH dependence in its fluorescence intensity, the tips were washed several times with 50% ethanol (pH ~7) before imaging to have the same solvent environment across all images. However, tips exposed to more viscous solvents SDS and Tween 20 (pH ~8) show slightly higher intensities even after these washes. FIG. 14 shows three fluorescent images of FITC-PEG-lipid modified fibers of varying fluorescent intensity. FIG. 14A shows a tip exposed to the loading solvent –50% ethanol, FIG. 14B shows a tip exposed to 0.1% Tween-20, and FIG. 14C shows a tip exposed to 50% ACN, where some of the lipid was removed. For the first nine test solvents, no statistical difference was observed in mean intensity. Due to the strong hydrophobic interaction of the lipid tail with the polypropylene fiber surface, 50% ACN and hexanes were able to only remove around 40 percent on adsorbed lipid. Overall, commonly used chromatography solvents should not affect the PEG-lipid surface modification.

Results showed that under a concentration range from 0.005 to 3 mg mL$^{-1}$ the adsorption isotherm remained linear, highlighting the rapid mass transfer and efficient fluid movement advantages of the capillary-channeled fibers. Varying the flow rate further highlighted these advantages due to only a small variation in breakthrough volume from 0.15 to 1 ml min$^{-1}$. The 1.8 mg g$^{-1}$ maximum binding capacity, found at 0.6 ml min$^{-1}$ of 3 mg ml$^{-1}$ FITC-PEG-lipid, was small when compared to other affinity ligand stationary phases. While this is expected, the physical properties of the fibers allow them to perform at much higher linear velocities and, with their favorable mass transfer and low backpressures, are likely to exhibit higher throughput and yield then other stationary phases. Lastly, the PEG-lipid surface modification remained stable after exposure to several test solvents, with only 50% ACN and hexanes able to disrupt the surface. This showed that the PEG-lipid modified fibers were chemically robust.

While embodiments of the disclosure has been described using specific terms, such description is for illustrative purposes only, and it is to be understood that changes and variations may be made without departing from the spirit or scope of the disclosure.

What is claimed is:

1. A surface modified solid phase for a chromatography separation protocol comprising:
a polymeric solid phase comprising a hydrophobic surface;
a lipid, the lipid including a hydrophobic end and a headgroup opposite the hydrophobic end, the hydrophobic end having the structure of:

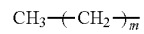

wherein m is from 6 to 30, the hydrophobic end being adsorbed to the hydrophobic surface of the polymeric solid phase such that the hydrophobic end of the lipid lays along or intercollates into the hydrophobic surface, the headgroup comprising a functional group that is configured for binding a targeted analyte, the functional group including a coenzyme, a nucleotide, or a polypeptide.

2. The surface modified solid phase of claim 1, wherein the lipid is a phospholipid, a glycerolipid, a glycerophospholipid, or a fatty acid.

3. The surface modified solid phase of claim 1, further comprising a hydrophilic spacer between the hydrophobic end and the headgroup.

4. The surface modified solid phase of claim 3, wherein the hydrophilic spacer comprises a polyethylene glycol spacer.

5. The surface modified solid phase of claim 1, wherein the polymeric solid phase comprises a fiber.

6. The surface modified solid phase of claim 5, wherein the fiber is a capillary-channeled fiber.

7. The surface modified solid phase of claim 1, wherein the polymeric solid phase comprises a polyolefin, a polyester, a polyaniline, a polylactic acid, a polyamide, a poly(styrene-divinyl benzene), a methacrylate, a polymer blend and/or a copolymer thereof.

8. A chromatography separation device comprising the surface modified solid phase of claim 1 held in a casing.

9. The chromatography separation device of claim 8, wherein the casing comprises an interior that is surface modified with the lipid adsorbed thereto.

* * * * *